(12) United States Patent
Ortega et al.

(10) Patent No.: US 8,111,165 B2
(45) Date of Patent: Feb. 7, 2012

(54) ACTIVE ON-PATIENT SENSOR, METHOD AND SYSTEM

(75) Inventors: Giovani M. Ortega, Arlington, VA (US); Michael J. Sciarra, Fairfield, CT (US)

(73) Assignee: Orthocare Innovations LLC, Oklahoma City, OK (US)

( * ) Notice: Subject to any disclaimer, the term of this patent is extended or adjusted under 35 U.S.C. 154(b) by 783 days.

(21) Appl. No.: 11/934,054

(22) Filed: Nov. 1, 2007

(65) Prior Publication Data

US 2008/0278336 A1 Nov. 13, 2008

Related U.S. Application Data

(63) Continuation of application No. 10/263,380, filed on Oct. 2, 2002, now abandoned.

(51) Int. Cl.
*G08B 23/00* (2006.01)
(52) U.S. Cl. ............. 340/573.5; 340/573.1; 340/539.12; 340/539.1; 340/539.11; 600/300; 600/301
(58) Field of Classification Search .................. 340/506, 340/573.5, 573.1, 539.12, 539.1, 539.11, 340/825.36, 825.49; 128/903–905, 920; 600/300, 301
See application file for complete search history.

(56) References Cited

U.S. PATENT DOCUMENTS

| 3,949,388 | A | 4/1976 | Fuller |
|---|---|---|---|
| 3,974,491 | A | 8/1976 | Sipe |
| 4,080,653 | A | 3/1978 | Barnes, Jr. |
| 4,175,263 | A | 11/1979 | Triplett |
| 4,450,431 | A | 5/1984 | Hochstein |
| 4,554,930 | A | 11/1985 | Kress |
| 4,610,253 | A | 9/1986 | Rosenberg |
| 4,633,237 | A | 12/1986 | Tucknott |
| 4,647,918 | A | 3/1987 | Goforth |
| 4,673,923 | A | 6/1987 | Boscoe |
| 4,692,747 | A | 9/1987 | Wolf |
| 4,813,436 | A | 3/1989 | Au |
| 4,839,512 | A | 6/1989 | Speck |
| 4,858,620 | A | 8/1989 | Sugarman |

(Continued)

OTHER PUBLICATIONS

Allen, V., et al., "Potential for Bed Sores Due to High Pressures: Influence of Body Sites, Body Position, and Mattress Design," British Journal of Clinical Practice 47(4):195-197, Jul./Aug. 1993.

(Continued)

*Primary Examiner* — Daryl Pope
(74) *Attorney, Agent, or Firm* — Christensen O'Connor Johnson Kindness, PLLC

(57) ABSTRACT

A sensor (which could be detachable) to sense a condition (including pressure from body weight or moisture from incontinence; applied by adhering to skin of a human body or by putting a diaper on the human body, for example), a signal processing circuit, a periodic or continuous transmitter, and a power supply (typically including a battery) are associated with a flexible substrate in low profile enabling disposition adjacent the human body. A transmitter antenna is on the substrate. Insulator film between battery contacts and a switch-and-transistor combination are two power-on techniques. A bedside monitor, a transceiver configured to receive signals from and transmit signals to the bedside monitor, and a computer connected with the transceiver can be included. Other features include: notification signaling; differently responsive antennas; unique identification; low battery detection; anti-collision transmission; patient protocol scheduling; local data transfer from the bedside monitor; and out-of-range transmission detection.

27 Claims, 9 Drawing Sheets

U.S. PATENT DOCUMENTS

| | | | |
|---|---|---|---|
| 4,944,060 | A | 7/1990 | Perry |
| 5,005,577 | A | 4/1991 | Frenkel |
| 5,010,772 | A | 4/1991 | Bourland |
| 5,047,750 | A | 9/1991 | Hector |
| 5,103,210 | A | 4/1992 | Rode |
| 5,184,112 | A | 2/1993 | Gusakov |
| 5,224,469 | A | 7/1993 | Mocny |
| 5,253,656 | A | 10/1993 | Rincoe |
| 5,291,181 | A | 3/1994 | DePonte |
| 5,307,818 | A * | 5/1994 | Segalowitz ............. 600/509 |
| 5,323,650 | A | 6/1994 | Fullen |
| 5,353,012 | A | 10/1994 | Barham |
| 5,410,297 | A | 4/1995 | Joseph |
| 5,510,770 | A | 4/1996 | Rhoads |
| 5,542,136 | A | 8/1996 | Tappel |
| 5,561,412 | A | 10/1996 | Novak |
| 5,566,479 | A | 10/1996 | Gray |
| 5,571,973 | A | 11/1996 | Taylot |
| 5,574,431 | A | 11/1996 | McKeown |
| 5,608,379 | A | 3/1997 | Narlow |
| 5,628,230 | A | 5/1997 | Flam |
| 5,642,096 | A | 6/1997 | Leyerer |
| 5,694,952 | A | 12/1997 | Lidman |
| 5,699,038 | A | 12/1997 | Ulrich |
| 5,745,036 | A | 4/1998 | Clare |
| 5,754,110 | A | 5/1998 | Appalucci |
| 5,769,784 | A | 6/1998 | Barnett |
| 5,841,350 | A | 11/1998 | Appalucci |
| 5,941,836 | A | 8/1999 | Friedman |
| 6,011,477 | A | 1/2000 | Teodorescu |
| 6,030,351 | A | 2/2000 | Schmidt |
| 6,031,791 | A | 2/2000 | Thoni |
| 6,053,873 | A | 4/2000 | Govari |
| 6,117,077 | A * | 9/2000 | Del Mar et al. ............. 600/301 |
| 6,129,686 | A | 10/2000 | Friedman |
| 6,147,592 | A | 11/2000 | Ulrich |
| 6,287,253 | B1 | 9/2001 | Ortega |
| 6,292,102 | B1 | 9/2001 | Smith |
| 6,362,725 | B1 | 3/2002 | Ulrich |
| 6,384,728 | B1 | 5/2002 | Kanor |
| 6,486,588 | B2 * | 11/2002 | Doron et al. ............. 310/322 |
| 7,149,733 | B2 * | 12/2006 | Lin et al. ............. 1/1 |

OTHER PUBLICATIONS

Bader, D. L., et al., "Effect of Externally Applied Skin Surface Forces on Tissue Vasculature," Archives of Physical Medicine and Rehabilitation 67(11):807-811, Nov. 1986.

DRI Sleeper®, Urocare Products, Inc., Pomona, California, n.d., <www.dri-sleeper.com>, as early as 1997.

Eriksson, E., "Etiology: Microcirculatory Effects of Pressure," in M. B. Constantian (ed.), Pressure Ulcers: Principles and Techniques of Management, Little, Brown, Boston, 1980, pp. 7-21.

Linder, R. M., et al., "The Prevention of Pressure Sores," Surgical Rounds, Jun. 1983, pp. 42-48 and 55.

Malem® Enuresis Alarms, Malem Medical, Lowdham, U.K., n.d., <www.malem.co.uk/home.htm> [retrieved Jan. 20, 2003].

Nytone® Enuretic Alarm, Nytone Medical Products, Salt Lake City, Utah, n.d., <www.nytone.com/prodinfo.html>, as early as Jul. 1974.

Patterson, R. P., and L. C. Stradal, "Technical Note: Warning Device for the Prevention of Ischaemic Ulcers in Patients Who Have Injured the Spinal Cord," Medical and Biological Engineering 11:504-505, Jul. 1973.

Personal Awareness Device [enuresis alarm], Nature Calls Marketing Corp., Saskatoon, Canada, <www.naturecalls.sk.ca>, as early as 1999.

Oxford Pressure Monitor, Talley Pressure Monitor, and Talley SD.500 Skin Pressure Evaluator, Talley Group Limited, Lansing, Michigan (believed to be published or in public use or on sale prior to Jun. 1998).

Pressore™ Monitor, Cleveland Medical Devices Inc., Cleveland, Ohio (believed to be published or in public use or on sale as early as Oct. 1995).

Remsburg, R. E., and R. G. Bennett, "Pressure-Relieving Strategies for Preventing and Treating Pressure Sores," Clinics in Geriatric Medicine 13(3):513-529, Aug. 1997.

Reswick, J. B., and J. E. Rogers, "Experience at Rancho Los Amigos Hospital With Devices and Techniques to Prevent Pressure Sores," in R. M. Kennedy et al. (eds.), Bedsore Biomechanics, University Park Press, Baltimore, 1976, pp. 302-310.

Robertson, J. C., et al., "An Interface Pressure Sensor for Routine Clinical Use," Engineering in Medicine 9(3):151-156, Jul. 1980.

Roemer, R., et al., "Technical Note: Warning Device for the Prevention of Ischaemic Ulcers in Quadriplegics," Medical and Biological Engineering, Sep. 1976, pp. 580-581.

Samaun, S., et al., "An IC Piezoresistive Pressure Sensor for Biomedical Instrumentation," IEEE Transactions on Biomedical Engineering 20(2):101-109, Mar. 1973.

SleepDry® Bedwetting Device, Starchild Labs Corporation, Aptos, California, <http://www.grogans.com/research.jsp?documentid=63>, as early as Dec. 1986 [retrieved Dec. 18, 2007].

Tamura, T., et al., "A Warning Detector for Urinary Incontinence for Home Health Care," Biomedical Instrumentation & Technology 29(4):343-349, Jul./Aug. 1995.

Werner, P., and I. Perkash, "Warning Mat to Signal Air Seat Cushion Failure," Archives of Physical Medicine and Rehabilitation 63(4):188-190, Apr. 1982.

Wet-No-More®, Travis International, Inc., Coos Bay, Oregon, <www.travisinternational.com>, as early as Sep. 18, 2002.

Wet-Stop®: The World's Best Bedwetting Alarm, Palco Laboratories, Palo Alto, California, n.d., <www.palcolabs.com> (believed to be published or in public use or on sale as early as Apr. 1978).

* cited by examiner

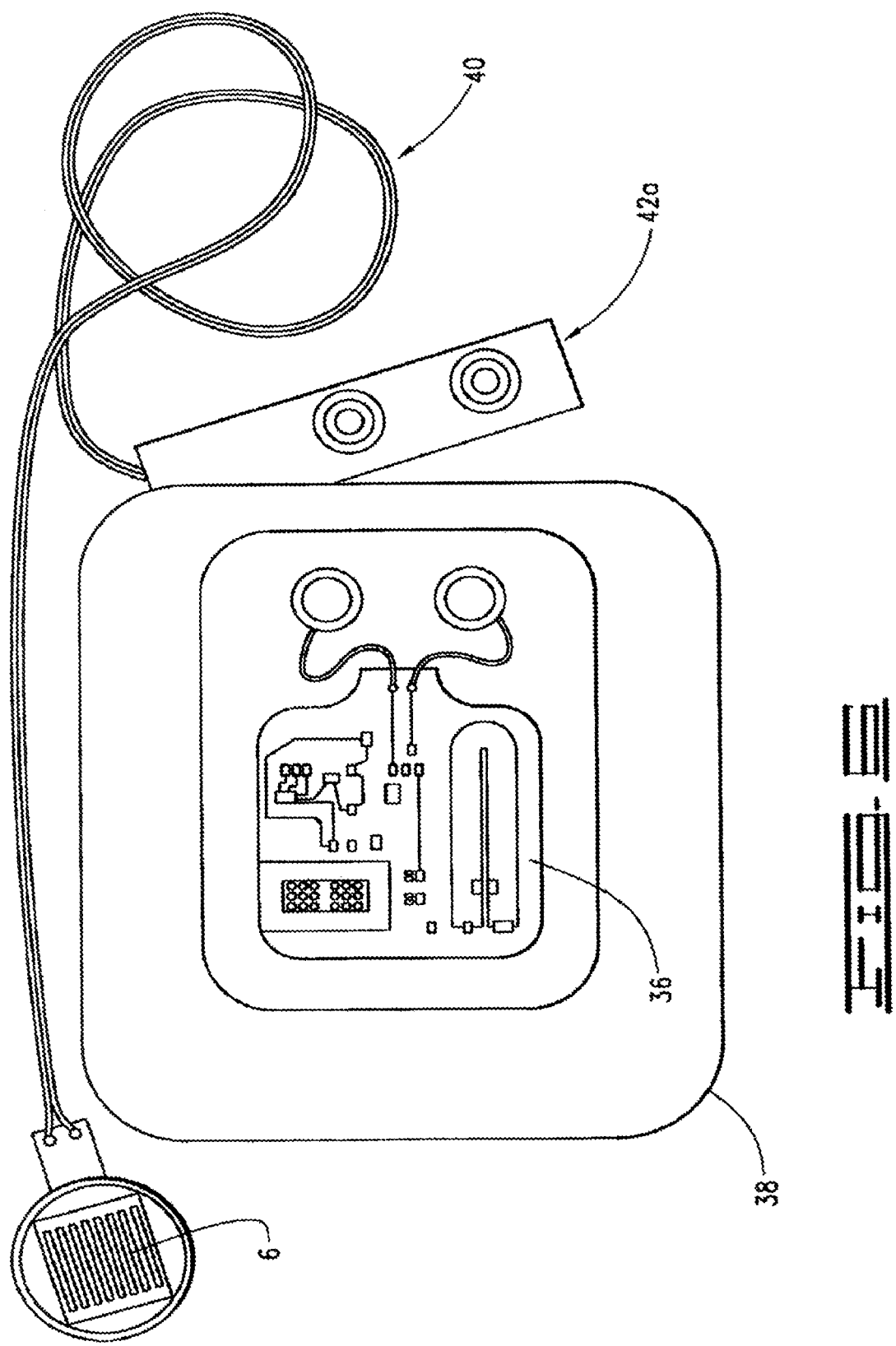

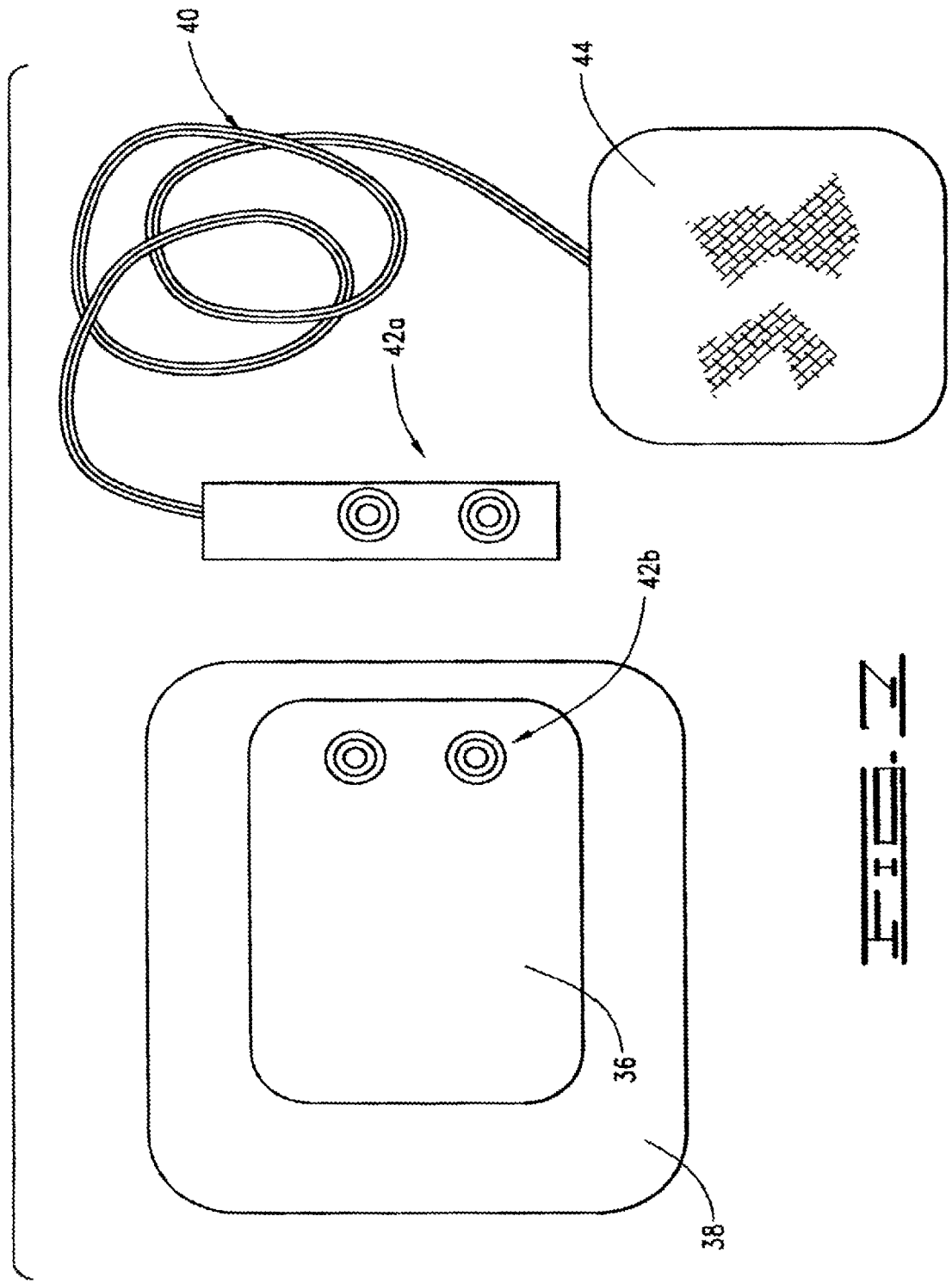

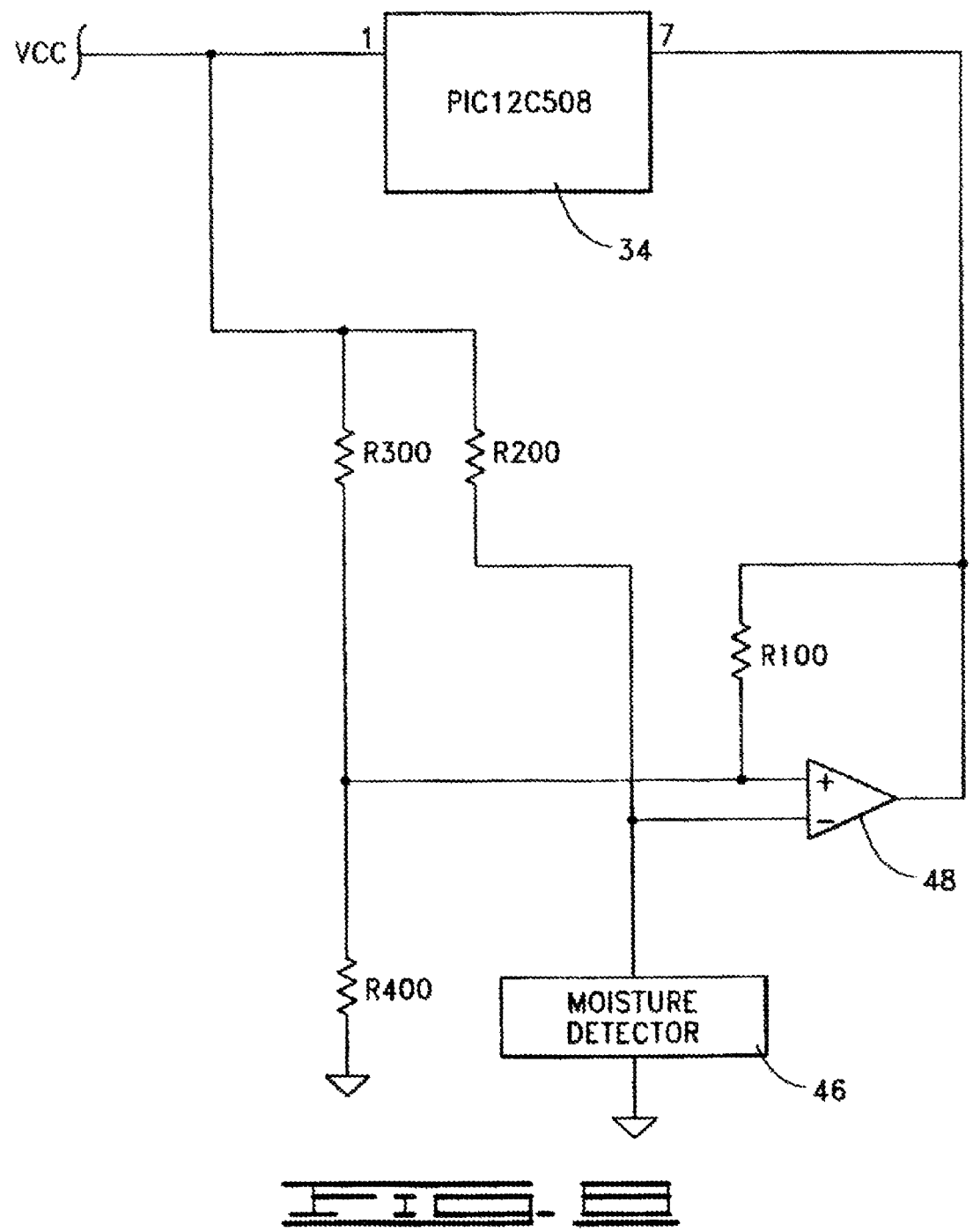

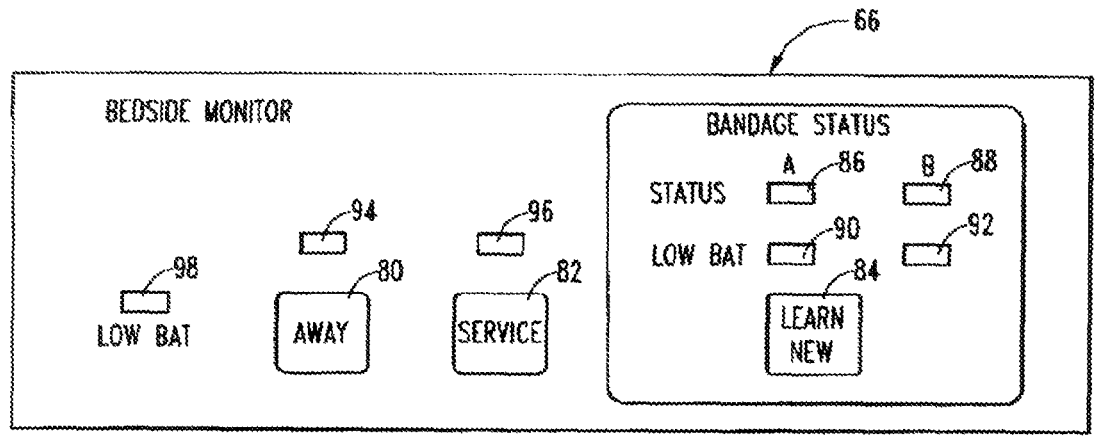
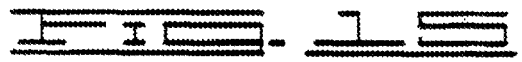
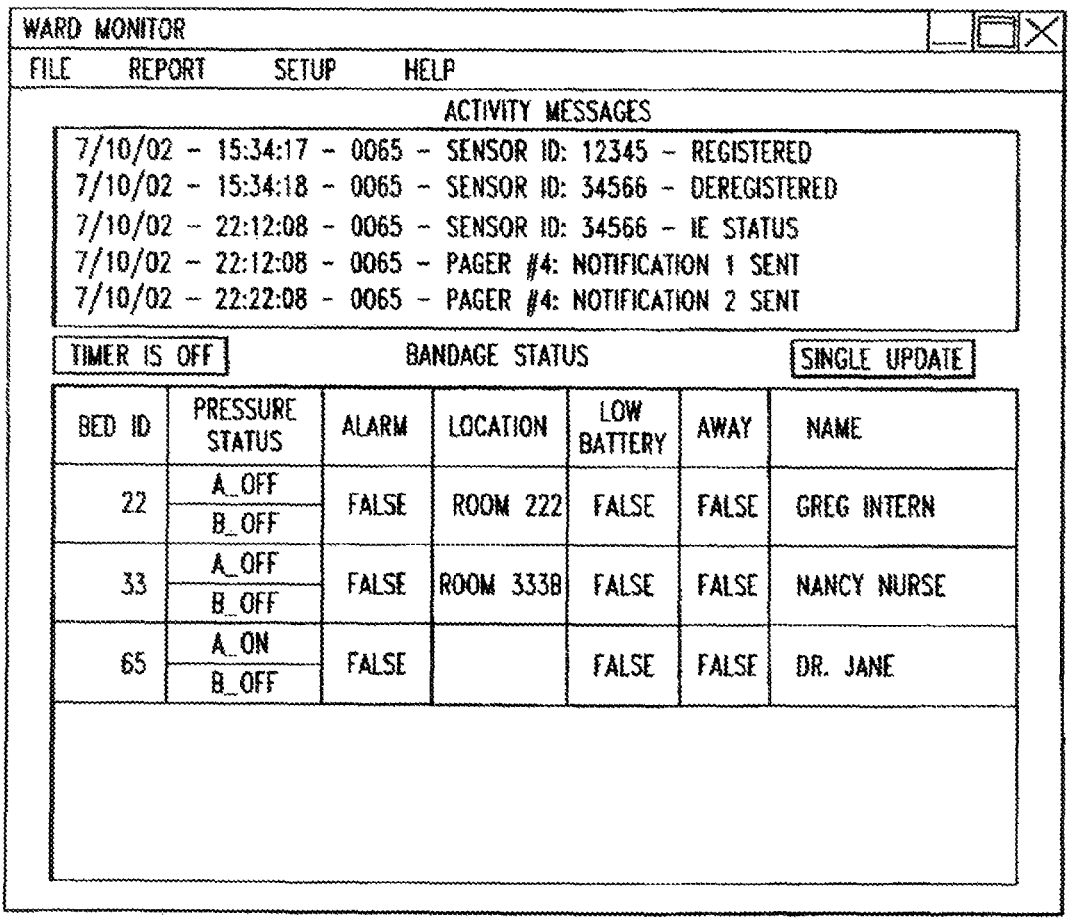
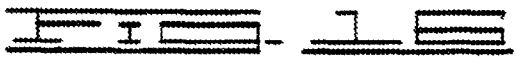

ACTIVE ON-PATIENT SENSOR, METHOD AND SYSTEM

CROSS-REFERENCE TO RELATED APPLICATION

This application is a continuation of application Ser. No. 10/263,380, filed Oct. 2, 2002, which is incorporated by reference herein.

BACKGROUND OF THE INVENTION

This invention relates generally to sensing conditions related to a human body and more particularly to sensing conditions that pertain to the care or well-being of a person who is confined to a bed or other sedentary position or who is incontinent. It also relates to providing notification in response to such sensing, which notification can be sent to the person whose conditions are being sensed or to others such as health care providers, for example. Two specific applications of the present invention that can be used separately or together relate to a medical sensor and a system and method of monitoring (1) one or more pressure sensitive areas of a human body and (2) dry/wet conditions adjacent a human body.

Although aspects of the present invention have application with regard to other human body conditions, the invention will be specifically described in the contexts of (1) pressure that contributes to the development of external skin ulcers (e.g., decubitus ulcers) and (2) wetness that occurs as a result of urinary or fecal incontinence, which can also contribute to pressure ulcer formation as well as to skin ailments such as dermatitis, etc. The invention also relates to a computer-implemented management system and method within the contexts mentioned above. The management system utilizes the number of episodes of the sensed conditions and times at which the sensed conditions occurred to formulate care protocols associated with pressure ulcer and incontinence treatment and/or prevention.

Pressure ulcers can develop in a person who is bedridden or confined to a wheelchair, for example. Intrinsic and extrinsic factors may be involved in the development of such pressure ulcers. Intrinsic factors include impaired mobility, incontinence, skin condition, nutrition, and mental status.

Exposure to pressure is one extrinsic factor. When a bony, protuberant body portion, for example, is pressed against a support such as a bed or a chair under the person's weight or part of that weight, pressure is applied to that portion. If this position is maintained for prolonged periods of time, such as due to the person's immobility, this prolonged pressure can be at least one contributing factor in causing a break in the person's skin, reduced blood flow to that tissue and the loss of surface tissue and the disintegration and necrosis of epithelial tissue (i.e., an ulcer)

Implementation of guidelines set forth by the Agency for Healthcare Research and Quality (AHRQ) has demonstrated that with diligent nursing care, many pressure ulcers are preventable. However, with staff/patient ratios typically found in nursing homes, it may be impractical to expect all aspects of the AHRQ guidelines to be followed for all but high-risk patients. The extent of this problem may grow as medical advances prolong the life expectancy of seriously ill patients and as the population over the age of 65 expands. In view of the foregoing, and as an increased number of patients are given home care, there is the need for cost effective and simple techniques and low cost equipment for pressure ulcer prevention and/or reduced healing time through improved patient monitoring methods.

Various equipment has been proposed or used in trying to prevent or treat pressure ulcers. This equipment includes overlays, replacement mattresses, and specialty beds that attempt to reduce the amount of pressure to which tissues are exposed. These vary in effectiveness, practicality of use, cost, and maintenance requirements. Although pertinent to the prevention and treatment of pressure sores, this particular equipment is distinct from the sensing and monitoring equipment and methods to which the present invention is directed.

Pressure sensing and monitoring systems have been proposed in, for example, U.S. Pat. No. 6,287,253 to Ortega et al., U.S. Pat. No. 4,554,930 to Kress and U.S. Pat. No. 5,253,656 to Rincoe et al. Another device, a Tekscan® (Tekscan, Inc. South Boston, Mass.) body pressure measurement system, monitors pressure. Other pressure analyzers have been available from Talley and Cleveland Medical Devices.

As mentioned, incontinence can also affect a person's susceptibility to decubitus ulcers, as well as to skin rashes and dermatitis, and the result of incontinence alone affects the person's immediate comfort. Thus, monitoring such as for whether an area adjacent the person is dry or wet is desirable.

Although there have been proposals and implementations addressing the general issue of human body monitoring and the specific issues of pressure and incontinence monitoring, there is still the need for novel and improved equipment and methods for sensing and monitoring one or more conditions related to the health of the human body and especially related to the development, prevention and treatment of pressure ulcers and to the detection of episodes of incontinence. There is also the need for a related computer-implemented management system and method. These preferably should facilitate the acquisition of, and notification in response to, pressure, moisture and time information that can be used in the prevention or treatment of pressure ulcers, other skin ailments, or otherwise in the care of human beings.

SUMMARY OF THE INVENTION

The present invention overcomes the above-noted and other shortcomings of the prior art by providing a novel and improved on-patient sensor and method and system related to monitoring and responding to one or more human body conditions. The present invention provides apparatus to sense a condition adjacent a human body, a method of sensing a condition adjacent a human body, a patient monitoring system, a method of monitoring a patient, and notification in response to such sensing or monitoring.

The present invention provides apparatus to sense a condition adjacent a human body, comprising: a sensor to sense a condition (including pressure from body weight and moisture from incontinence, for example) adjacent a human body; a signal processing circuit to which the sensor connects; a transmitter connected to the signal processing circuit; a power supply connected to provide electricity for operation of the sensor, the signal processing circuit, and the transmitter; and a flexible printed circuit substrate having at least the signal processing circuit, the transmitter, and the power supply mounted thereon in low profile enabling disposition of the apparatus adjacent a human body. In some embodiments the sensor is detachable. The sensor can be single-mode or multiple-mode, such as one that responds to both pressure and moisture.

Another definition of the present invention is as apparatus to sense a condition adjacent a human body, comprising: a sensor to sense a condition adjacent a human body; a transmitter configured to operatively associate with the sensor to transmit a signal digitally encoded with a unique identifier responsive to the sensor, the transmitter including an antenna; and a flexible substrate having the antenna disposed thereon and connected with the sensor and transmitter in low profile enabling disposition of the apparatus adjacent a human body. A battery can be mounted on the flexible substrate for providing electricity to operate the sensor and the transmitter, and a low battery detector can be included (as well as can other features).

The present invention can also be stated as apparatus to sense a condition adjacent a human body, comprising: a sensor to sense a condition adjacent a human body; a transmitter configured to operatively cooperate with the sensor to transmit a signal responsive to the sensor; a power supply for providing electricity to operate to the sensor and the transmitter, wherein the power supply includes a removable insulator film and a battery having a terminal initially electrically isolated from the sensor and transmitter by the insulator film such that the apparatus is energized by the battery upon pulling the insulator film out; and a flexible printed circuit substrate having at least the transmitter and the power supply mounted thereon in low profile enabling disposition of the apparatus adjacent a human body. In another implementation the power supply includes a switch and transistors connected for maintaining a powered on state upon a one-time closure actuation of the switch.

The present invention also provides a method of sensing a condition adjacent a human body, comprising: disposing in low profile adjacent a human body, by adhering to skin of the human body or by putting a diaper on the human body, apparatus to sense a condition adjacent the human body, the apparatus including a sensor, a transmitter, a power supply, and a flexible substrate having at least the transmitter and the power supply connected thereto in low profile enabling disposition of the apparatus adjacent a human body; energizing the apparatus solely with the battery; sensing a condition using the sensor; and transmitting a wireless link signal from the transmitter in response to the sensed condition. Among other steps that can be included are steps of storing unique identification data in the apparatus and transmitting a signal in response to the stored unique identification data. Transmitting can be performed periodically or continuously.

The present invention still further provides a patient monitoring system, comprising: a sensing apparatus including a sensor, a transmitter responsive to the sensor, a power supply, and a low profile flexible substrate having at least the transmitter and the power supply connected thereto; a bedside monitor configured to receive signals transmitted from the transmitter such that the sensing apparatus and the bedside monitor are in wireless communication, the bedside monitor including a first transceiver; a second transceiver configured to receive signals from and transmit signals to the first transceiver such that the first transceiver and the second transceiver are in wireless communication with each other; and a computer connected in communication with the second transceiver. Remote signaling can be provided, such as via a paging system responsive to control from the computer. The bedside monitor can include a plurality of differently responsive antennas to prevent null transmission spots from adversely affecting the wireless communication. The bedside monitor can include encoded signals defining an identification code for the bedside monitor, and the bedside monitor can include means for receiving and storing identification data from the sensing apparatus.

The present invention also provides a method of monitoring a patient, comprising: connecting a condition sensing apparatus to a patient, including performing at least one from the group consisting of adhering a flexible substrate of the condition sensing apparatus to skin of the patient and putting diapers having the flexible substrate on the patient, the flexible substrate having a sensor, a transmitter and a battery connected thereto; collecting data transmitted from the condition sensing apparatus when the condition sensing apparatus senses a pressure or incontinence condition adjacent the patient; and replacing the sensor of the condition sensing apparatus, including disconnecting the sensor from the condition sensing apparatus and connecting a replacement sensor thereto such that the flexible substrate, the transmitter and the battery are reused. Other steps that can be included in the foregoing or other definitions of the present invention include one or more (that is, they can be used individually or in combinations) of the following: transmitting from the condition sensing apparatus such that signal collision with transmissions from other condition sensing apparatus on the patient is avoided; using the collected data to generate care protocol scheduling for the patient; maintaining and updating remote from the condition sensing apparatus data identifying the condition sensing apparatus; transmitting data from the condition sensing apparatus to a bedside monitor and locally transferring data from the bedside monitor to a data collection unit; receiving through any of a plurality of diversity antennas a transmission from the condition sensing apparatus; detecting in-range and out-of-range transmission conditions relative to the condition sensing apparatus; and sending, in response to the collected data, a control signal through the operation of which the patient is notified of the pressure or incontinence condition.

Therefore, from the foregoing, it is a general object of the present invention to provide a novel and improved on-patient sensor and method and system related to monitoring and responding to one or more human body conditions. Other and further objects, features and advantages of the present invention will be readily apparent to those skilled in the art when the following description of the preferred embodiments is read in conjunction with the accompanying drawings.

BRIEF DESCRIPTION OF THE DRAWINGS

FIG. 6 illustrates a sensing apparatus mounted on a wound dressing but with a detachable sensor.

FIG. 7 illustrates another view of the embodiment of FIG. 6 but with the detachable sensor embedded in a pad.

FIG. 8 is a schematic circuit diagram of an embodiment of a moisture sensor for a sensing apparatus of the present invention.

FIG. 9 is a plan view of a structural embodiment of a sensing apparatus incorporating the moisture sensor of FIG. 8.

FIG. 10 is an edge view of the low profile embodiment of FIG. 9.

FIG. 15 is an exterior view illustration for an embodiment of a local (e.g., bedside) monitor of the system of FIG. 14.

FIG. 16 represents a computer display as one illustration of an operator/computer interface for a computer of the system of FIG. 14.

DETAILED DESCRIPTION OF THE INVENTION

Figure 1:
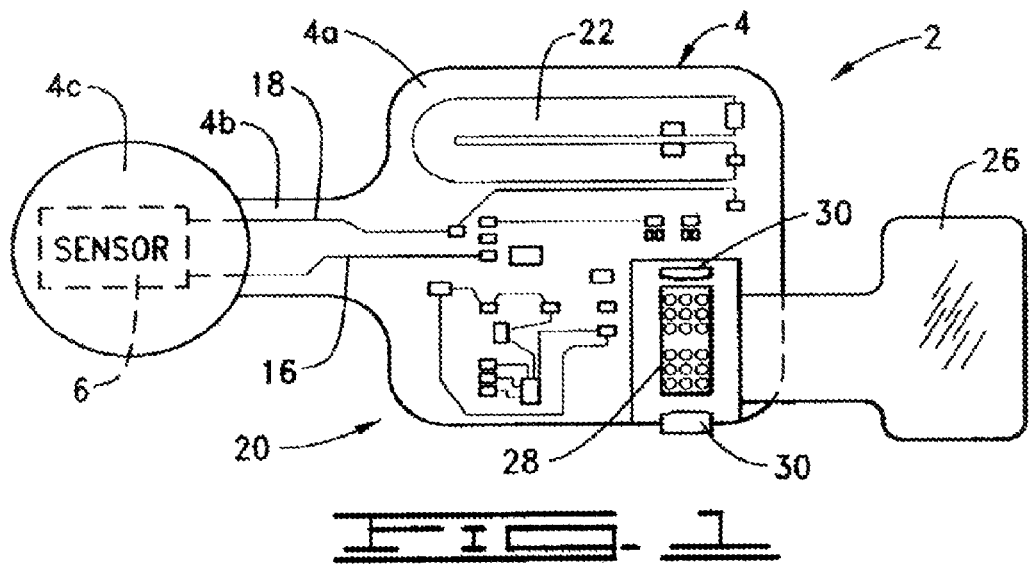
FIG. 1 is a plan view of one implementation of a sensing apparatus in accordance with the present invention.
Figure 2:
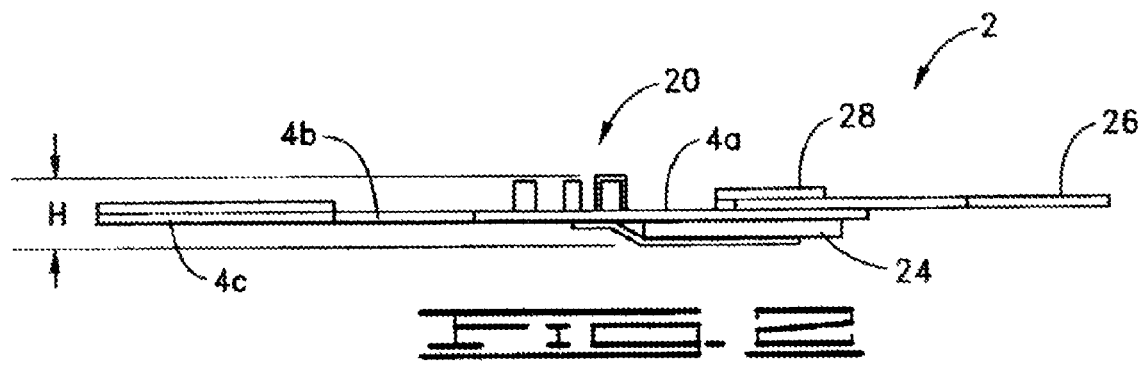
FIG. 2 is an edge view exemplifying a low profile feature of the sensing apparatus of the present invention.
Figure 3:
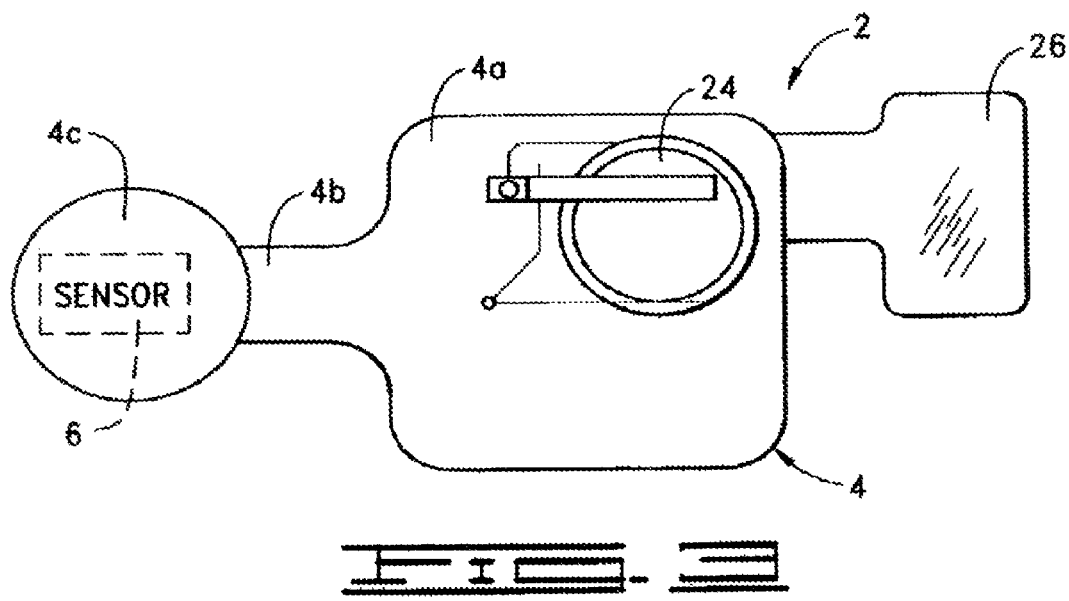
FIG. 3 is a view of the sensing apparatus from beneath the view of FIG. 1.

An implementation of an apparatus 2 to sense a condition adjacent a human body in accordance with the present invention is illustrated in FIGS. 1-3. This sensing apparatus 2 is preferably an active device in the sense that it contains its own internal power supply. This embodiment is, and other embodiments desirably are, low profile and flexible to conform to the exterior of human body. Such low profile refers to the thinness exhibited in FIG. 3 as dimension "H". In general, the sensing apparatus 2 can be implemented using analog or digital electronics technology (including a combination of both).

The illustrated embodiment of FIGS. 1-3 includes a flexible printed circuit substrate 4 having other components described below mounted on it in a manner to obtain the low profile (small "H") characteristic of the invention, which is one feature enabling disposition of the apparatus 2 adjacent a human body. Such disposition can be in any suitable manner, including directly to a person's skin or as an integral or after-connected part of a bandage or diapers or other clothing article intended to be worn by a person. The substrate 4 is preferably flexible, as mentioned, and is preferably made of a suitable material to provide such flexibility as well as other desirable characteristics of a printed circuit substrate. For example, one type of material is Kapton® polyimide from DuPont. Another example is polyester on which the circuitry is provided using conductive silver ink that is silk-screened onto the thick film substrate.

Although not limiting of broader aspects of the present invention, the illustrated substrate has a rectangular main body portion 4a from which a narrower neck portion 4b extends to a circular free end portion 4c. In one particular implementation, the dimensions of the structure are as follows: the rectangular area 4a is 2.5 cm by 2.5 cm, circular area 4c is 2.0 cm in diameter, and the overall length is 5 cm; at the thinnest portion the substrate 4 is 0.25 mm and at the thickest (electronic components) 1.7 mm (that is, in this implementation H=1.7 mm). In general, "low profile" for the illustrated embodiments is less than about 2 mm. This dimension can be substantially less if the integrated circuits were adhered to the substrate in die form.

The circular portion 4c, which contains a pressure sensor 6 in this implementation, is extended from the rectangular portion 4a, which contains the majority of the electronic circuits and components. In other implementations the sensor portion 6 can be constructed such that it is located on substrate layers on top of the main substrate layer 4. In other words, the sensor portion 6 does not need to be on the same layer as the main substrate layer. To further explain, the substrate 4 may be composed of several layers, each adhered by a double-sided non-conductive adhesive layer such that circuits from one layer may be continued onto other substrate layers using conductive vias to connect separate circuits.

In general, the sensor of the sensing apparatus 2 can be of any type for sensing any condition that is related to a physical condition of a patient and that can be sensed and processed in accordance with the present invention. Two particular conditions for which apparatus are shown in the drawings are a pressure occurring in response to weight of the human body against a support and moisture occurring due to incontinence (for example, enuresis). A sensing apparatus can be a single-mode type dedicated to sensing a single condition, or it can be a multiple-mode sensing apparatus with which multiple conditions can be sensed. For example, as will be referred to below, a dual-mode sensing apparatus can respond to both pressure and moisture.

One type of a pressure sensor 6 of the implementation of FIGS. 1-3 is composed of two parts. The first part is made up of conductive traces printed onto substrate portion 4c adjacent to each other so that they do not contact each other. The second part is composed of a different substrate layer which has printed upon it a conductive layer. The substrate layers are positioned such that the two conductive surfaces face each other in opposition but are separated by a spacer ring (shown in FIG. 4 as reference number 12) that prevents the conductive layers from contacting each other when less than an actuation pressure is exerted on the external surfaces of the sensor. Each substrate layer is adhered to opposite surfaces of the spacer ring of this embodiment. Another example, shown in FIG. 4 (like reference numerals for like features are used in the different illustrated embodiments), includes conductive traces 8, 10 on the same surface of the substrate 4c but the substrate portion 4c is designed so that it folds onto itself to form the two opposing conductive trace layers (in the FIG. 4 implementation, the trace 8 has two electrically isolated parts 8a, 8b that are connected by the trace 10 when sufficient pressure is applied). Spacer ring 12 serves the same function as described above. An air vent 14 is formed at the portion of the spacer ring 12 adjacent the connecting substrate web between the two sections of substrate portion 4c. The air vent permits air within the chamber created by the substrate layers around the spacer ring 12 to be expelled when pressure is exerted to the exterior of the sensor 6. The required pressure or force exerted normally on these planar surfaces of the sensor 6 at which the interfacing conductive layers 8, 10 come into contact is controlled by design parameters of, for example: 1) substrate material thickness and rigidity; 2) spacer ring dimension and geometry; and 3) spacer ring thickness. One example of a combination of the parameters listed above can be such that the conductive layers come into contact in the presence of pressure of 10 mm Hg and above. This design example would indicate the presence of pressure below the broadly accepted pressure at which human capillary closure takes place: 32 mm Hg (millimeters of mercury). The ability to design for a specific "closure" pressure allows for sensing the presence of even lower pressures (for example 2 mm Hg) which can have clinical importance in that sometimes capillary closing pressures can be substantially lowered in the presence of a compromised vascular system brought about by conditions such as diabetes. In another example, there can also be a conductive interface layer, such as carbonized rubber, between the opposing substrates such that a signal processing circuit of the apparatus can detect a graduated change in electrical resistance resulting from graduated levels of pressure exerted on the exterior of the sensor surfaces. The sensor conductive layers can be deposited by suitable means onto the substrate, including for example, adhesion, etching, or printing. The conductive layer (such as copper, silver ink, carbon ink) can be formed into traces, which in turn, form electrical circuits. For the illustrated examples, a pair of laterally separated conductive traces 16, 18 from the electrical circuit on substrate portion 4a extend through substrate portion 4b to the conductors 8a, 8b, respectively, on the circular portion 4c of the substrate. If the conductor 10 is not pressed in contact with the traces 8a, 8b, the pair of conductive traces 8a, 8b contained within the circular portion of the substrate maintain an open electrical circuit that leads to the remainder of the electronic circuit.

The sensor 6 connects to a signal processing circuit mounted in suitable manner on the substrate. This circuit is generally indicated by the reference numeral 20 in the two embodiments of FIGS. 1-3 and FIG. 4. A particular implementation will be described below with reference to FIG. 5. In general, however, the signal processing circuit 20 performs at least signal interfacing between the raw signal from the sensor 6 and a signal in a form for storing or transmitting, for example. This can include processing in the analog domain or the digital domain (including in both). In a particular implementation, the signal processing circuit provides other data handling functions, including storing unique identification data (for example, a serial number) in the apparatus such that the data can be transmitted from the apparatus to identify it to other equipment, for example. Another example is to provide status information, such as a low battery condition as well as the information obtained from the sensor. The circuit can include lights, for example, such as to correspond to different species of sensing apparatus.

The illustrated sensing apparatus also comprises a transmitter connected to the signal processing circuit. The transmitter includes an antenna 22, which in the illustrated embodiments of FIGS. 1-4 is printed onto the substrate. The transmitter transmits a radio frequency (RF) signal to the antenna 22 which radiates this signal in response to the sensed condition.

The sensing apparatus further includes on-board the substrate a power supply connected to provide electricity for operation of the sensor, the signal processing circuit, and the transmitter. Such power supply is implemented in the illustrated embodiments by a battery (see battery 24 in FIG. 3 for that embodiment; one is similarly located for the FIG. 4 embodiment). These embodiments are energized solely by their respective battery, thereby making the embodiments fully active as compared with a passive energization technique, such as provided by an external electromagnetic field.

In the embodiment of FIGS. 1-3, the power supply includes a removable insulator film 26. The battery 24 has one of its terminals (the positive terminal in this illustrated embodiment) initially electrically isolated from the other circuitry by the insulator film 26 such that the apparatus is in a powered off condition until energized by the battery upon pulling the insulator film 26 out. When the insulator film 26 is pulled out, the previously isolated terminal of the battery 24 then moves into contact with the remainder of the circuit to be energized by the battery 24. In FIGS. 1-3, the positive battery terminal connects to a dimpled conductive strip (such as a copper strip) on the substrate 4. This strip is under dimpled conductive strip 28, shown in FIG. 1, which is connected to the other part of the electrical circuit. The insulator film 26 has an end disposed between these contacts. Shown in cutaway in FIG. I overlying strip 28 is clip 30 with spring action (such as a metal or plastic two-pronged inwardly biased clip); it clips the two strips to ensure that upon removal of the insulator film 26, the strip 28 is pressed and held against the underlying conductive strip whereby the remainder of the circuitry connected to the strip 28 is energized. Thus, the insulator film 26 defines a pull tab switch located between the positive battery terminal and the rest of the circuit in the embodiment of FIGS. 1-3. The tab removal is a one-time non-reversible procedure in this implementation.

Figure 4:
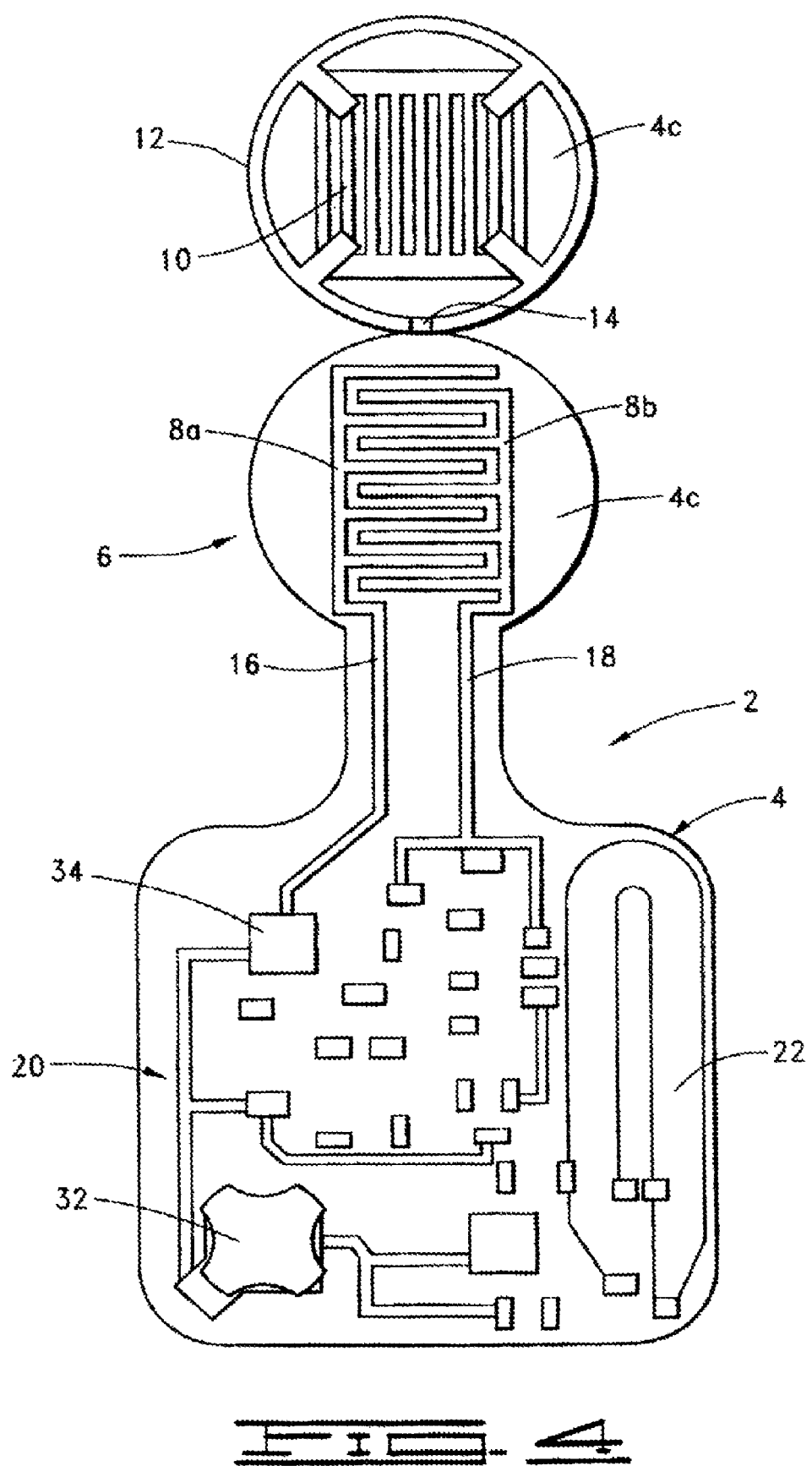
FIG. 4 is a plan view of another implementation of sensing apparatus of the present invention.

In the embodiment of FIG. 4, the electronic circuit is changed from a power-off condition to a power-on condition using a switch and transistor circuit that maintains the power-on condition after a one-time closure actuation of the switch. The switch in the FIG. 4 embodiment is a push actuated dome switch 32. Use of this dome switch provides for maintaining a low profile of the apparatus.

The foregoing can be used to implement a method of the present invention, comprising disposing in low profile adjacent a human body apparatus to sense a condition adjacent the human body. The apparatus includes a sensor, a transmitter, a power supply, and a flexible substrate having at least the transmitter and power supply connected to it in low profile, enabling disposition of the apparatus adjacent a human body. "Low profile" of the apparatus as used in this description and in the claims means sufficiently thin as to be comfortably used next to a human body, such as permitting disposition of the apparatus adjacent a human body by adhering it to skin of the human body (such as directly or on top of other films such as wound dressings or pads) or by putting it on or in a diaper on the human body. In the illustrated implementations of FIGS. 1-4, low profile is within a thickness or height of about 2 mm.

Figure 5:
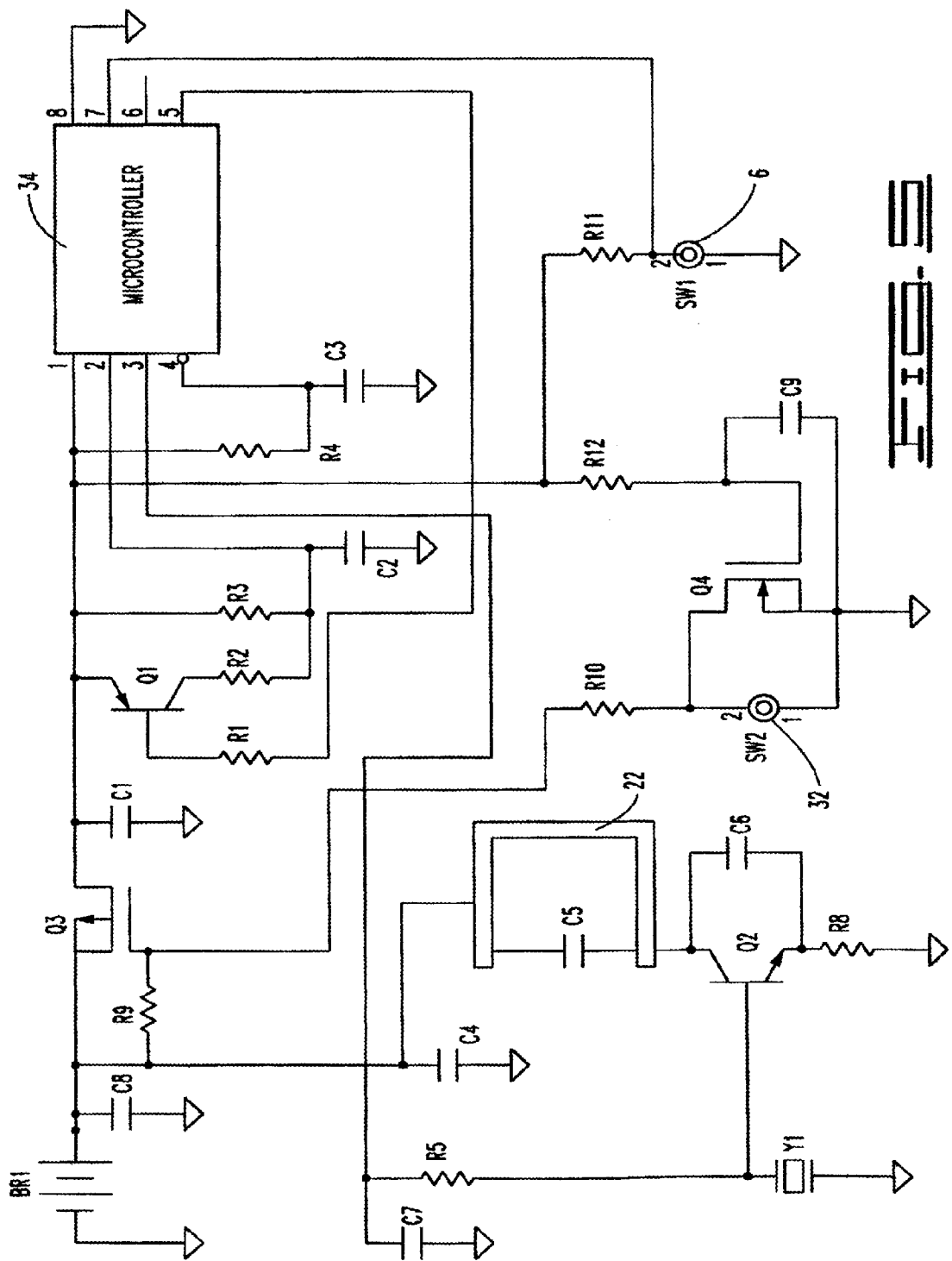
FIG. 5 is a schematic circuit diagram of an embodiment of a circuit for the sensing apparatus of the present invention.

A schematic circuit diagram for a particular implementation of circuitry for the FIG. 4 embodiment is shown in FIG. 5. This can be used in the embodiment of FIGS. 1-3, except that in FIG. 5 the pushbutton activation circuit is used instead of the pull tab configuration to turn-on the circuit.

Instead of using the insulator film 26 of FIGS. 1-3, the FIG. 5 circuitry uses the transistor Q3-Q4 circuit with switch SW2. Transistor Q3 is off until switch SW2 (a dome switch 32 in the particular implementation of FIG. 4) is pressed. Pressing SW2 turns on Q3 so that the battery 24 is connected to a microcontroller 34 (PIC12C508 in the illustrated implementation) and operation of pressure responsive sensor switch SW1 (the sensor 6 described above) can be detected. When SW2 is closed to turn on the sensing apparatus, transistor Q4 turns on to provide a short across SW2 to keep the sensing apparatus on regardless of the subsequent state of switch SW2, thereby providing a one-time turn-on switch of similar effect to the one-time pull tab provided by the insulator film 26 described above. Although the battery 24 remains connected in circuit, battery drain is minimal for the illustrated implementation.

Continuing in FIG. 5, transistor Q1 provides a clock signal to the microcontroller 34 in response to the pin 5 output from the microcontroller 34. The frequency generated to the microcontroller 34 is controlled by the embedded program and such that the switching action can place the microcontroller 34 in sleep mode thus conserving power between transmissions.

The microcontroller 34 performs signal processing in that it monitors the state of switch SW1 (the sensor 6) through pin 7 of the illustrated microcontroller 34. Switch SW1 is in one predetermined state (for example, one of either open or closed, but with open being used for the "no pressure" condition in the illustrated embodiments) when it is applied to a person and the person is not putting weight on SW1; it is in another predetermined state (for example, the other state from the first one mentioned; that is either closed or open) when the person puts pressure on it. SW1 can be implemented to provide two discrete signals (e.g., on and off) or to provide a continuous or a multiple level discrete signal to indicate different pressure levels being applied to it.

Still referring to FIG. 5, the circuit including crystal oscillator Y1 and the transistor Q2 provides the transmitter of this implementation. It responds to a modulation signal from pin 3 of the microcontroller 34. which signal modulates a 315 megahertz (MHz) carrier frequency provided by the particular components shown in the transmitter of FIG. 5. Transmissions can be provided through the antenna 22 as a radio frequency electromagnetic burst every few seconds, versus continuous transmission, to reduce battery use; however, other forms of transmission, including continuous, can be used. This transmitter can define or include a standing acoustic wave (SAW) resonator. To try to prevent simultaneous transmissions from multiple sensing apparatus 2 used on the same patient, for example, a transmission of data from a respective sensing apparatus 2 occurs during a time commencing pseudorandomly in a longer transmission window within an overall time during which a carrier "beacon" is transmitted. For example, a three-millisecond data transmission burst is sent within a twenty-millisecond window at the beginning of a carrier frequency transmission period. With pseudorandom commencement of these bursts, it is unlikely any two from different sensing apparatus will occur at the same time.

The implementation of FIG. 5, as embodied in the structural implementation of FIGS. 1-3 or 4, is particularly configured for sensing pressure at a point of application to a human body. A plurality of such sensing apparatus can be used concurrently to sense multiple locations on the body (the use of "a", or "an" element without an express numerical limitation thus encompasses one or more as used in this description and in the claims). In such an application, each apparatus must be externally distinguishable to allow correlation to the internal tracking and monitoring taking place during communication to other equipment. As an example, suppose a low battery indicator is engaged, the user must be able to understand to which (among several) apparatus the low battery indicator corresponds. An external labeling or marking of each apparatus such as by alphabetical symbols ("A", "B", "C", etc.) could provide a visual means of correlating the indicated low battery status to the appropriate apparatus on the human body. The receiving equipment must also provide a way to indicate the individual status—as will be discussed later. One attachment technique is to have the sensing apparatus form part of or be connected to a bandage or wound dressing that is to be applied to the desired location on the human body. Specific application is, for example, to actual or potential decubitus ulcer sites. In this context and for the particular components of FIG. 5, such a bandage unit has the 315 MHz transmitter whose carrier frequency is modulated by the control signal output by the microcontroller 34 in response to the pressure-indicating signal provided by operation of switch SW1. This implementation also includes a 32-bit identification code programmed into program memory of the microcontroller 34. The program under which the microcontroller 34 operates is a stand-alone program designed to periodically transmit the preferably but not limited to unique 32-bit bandage ID and includes five status bits, namely: 1) pressure switch closed (thereby indicating pressure is being applied to the location on the human body where the bandage is affixed), 2) low battery, 3) "A" selected, 4) "B" selected (reference to "A" and "B" are for a simple two bandage or sensor apparatus system in which only two are applied to the body, and 5) just powered on.

This program provides the following functionality. It initializes the microcontroller 34 or recovers from a reset. Initially, for the first minute after initial energization upon first closing of switch SW2, the sensing apparatus transmits, at a 1 kilohertz (KHz) modulation rate using ⅓, ⅔ ON-OFF-Keyed (OOK) modulation in a particular implementation, the ID and status bits. During this interval, the just-powered-on status bit is set (after one minute, the bit is cleared).

The program repeats the ID and status bits transmission at a pre-programmed interval of time (example, 30 seconds) until battery power fails.

The microcontroller 34 can be programmed to perform other functions as well. One non-limiting example is to program in a signal collision avoidance routine that pseudorandomly selects the time a transmission command is executed within a time frame. This approach decreases the chances that multiple sensing apparatus on a single patient transmit at the same time to one or more receivers.

The small and flexible apparatus of the present invention can be implemented in any of the following, for example: a) incorporated into wound dressing such that it is discarded along with the dressing, b) applied on top of a film or pad (such as a wound dressing) such that it does not directly contact the human body, c) applied on a human body without wound dressing, such as for patients who do not need bandaging, d) removable from the dressing and re-used or e) applied so that portions of the apparatus such as the sensor 6 are applied to one location of the human body while the remaining portions of the apparatus are adhered to a different location of the human body. In at least some implementations, the sensor is preferably detachable from the rest of the electronics package which can be re-used with a replacement sensor. This is illustrated in FIGS. 6 and 7, which show 1) primary electronics package 36 (such as the electronics portion on substrate portion 4a) embedded in wound dressing 38 and 2) detachable sensor portion 40 (such as including components of substrate portion 4c) that connects through mating snap connectors 42a, 42b. In FIG. 7 the sensor is embedded in a pad 44.

The foregoing specific use has been described with reference to sensing pressure. As mentioned, other conditions can be sensed. One example is to sense between dry and wet conditions, such as useful with an incontinent person. One embodiment of a moisture sensor that can be used with the circuitry of FIG. 5 in place of switch SW1 is schematically represented in FIG. 8, which shows the microcontroller 34 from FIG. 5 with moisture detector 46 connected to it in place of the pressure sensor switch SW1. The sensor status changes from "dry" to "wet" when the microcontroller 34 detects a change in voltage at the output of operational amplifier 48. Such change in voltage results from a relative change in resistance in the presence of moisture between the two adjacent yet isolated conductive traces in the moisture detector 46. When this voltage changes sufficiently to pass the threshold set at the other input to the operational amplifier 48, the operational amplifier output changes. Resistors R100, R300 and R400 in conjunction with the operational amplifier 48 regulate the triggering level.

FIGS. 9 and 10 illustrate one embodiment of physical construction for a moisture sensor apparatus using the components of FIGS. 5 and 8. This integrated sensor/transmitter of FIGS. 9 and 10 is designed for one-time use and is to be discarded with every diaper change, for example. Wicking material 50 (shown in FIG. 10 but not FIG. 9) provides a controlled absorbency to the printed traces defining the resistance of the moisture detector 46, thus eliminating false triggering due to humidity rather than incontinence wetness. The signal processing, transmitter and power supply components are in region 52 on the substrate 4 of this embodiment.

Figure 11:
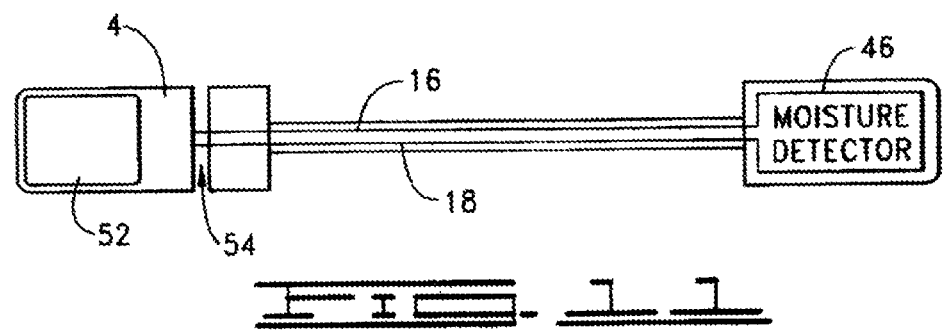
FIG. 11 is a plan view of another structural embodiment of a sensing apparatus incorporating the moisture sensor.

The sensor and transmitter of another configuration of sensing apparatus of the present invention are detachable as mentioned above. For the moisture sensor, this is represented in the particular illustration of FIG. 11, in which the moisture detector 46 is discarded with each diaper change but the other electronics of region 52 mounted on the flexible substrate 4 are retained and re-used. The electronics 52 mounted on substrate 4 can remain adhered or otherwise connected to the human body, diaper, or article of clothing. This configuration shows elongated leads embodying conductors 16, 18 (thus similarly labeled) from the sensor to the connector tab of the substrate 4. Contact connectors 54 (for example, stainless steel pins, clips, or mating snap connectors) connect the electronics to the sensor strip. The housing containing the electronics of region 52 is attachable and detachable to the exterior of the diaper. Although not pictured here, the moisture detector for this configuration also preferably uses wicking material. So, one can replace the sensor without replacing the transmitter or the battery or other circuits. This includes disconnecting the sensor from the transmitter and disposing the sensor after sensing the condition, and connecting another disposable sensor to the transmitter to sense a subsequent condition.

Figure 12:
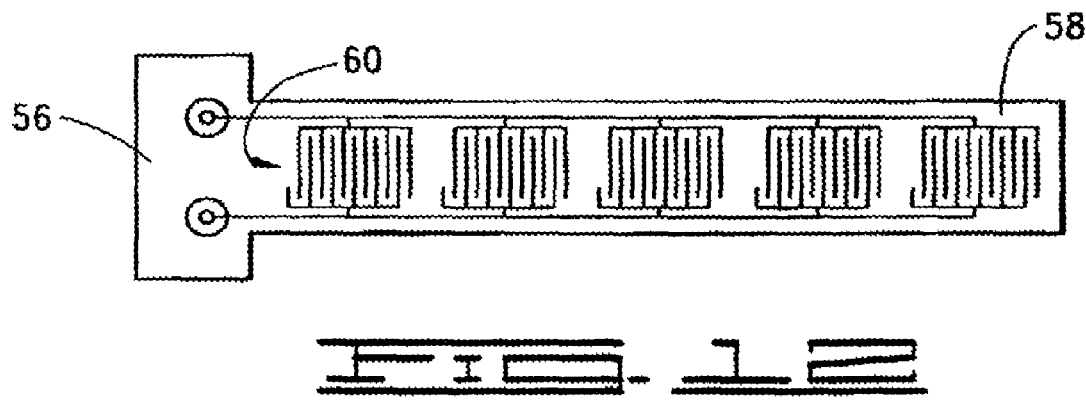
FIG. 12 is a plan view of a further structural embodiment of a moisture sensing apparatus of the present invention.
Figure 13:
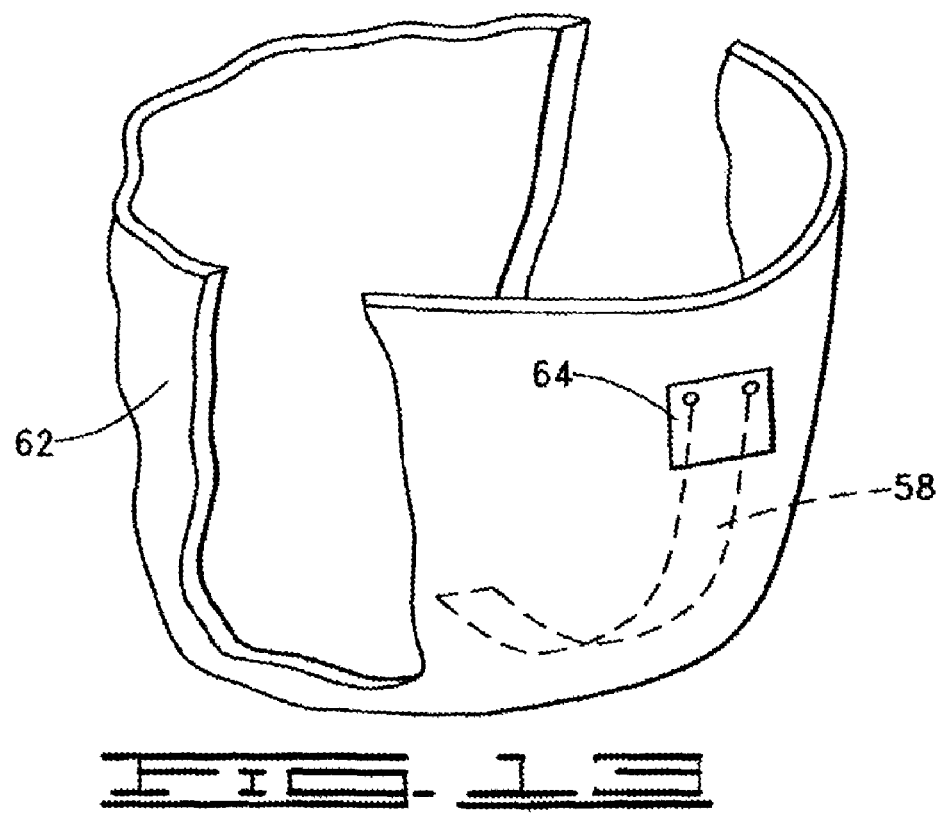

Another disposable, replaceable moisture detector is represented in FIG. 12. This embodiment includes a snap connector 56 as illustrated in the pressure sensor of FIGS. 6 and 7. Extending from the connector 56 end in FIG. 12 is a flexible sensor strip 58 having multiple moisture detector elements 60 disposed along the length of the strip. The detector elements 60 are schematically illustrated as interleaved but electrically separated conductive traces, which general structure is also shown in the FIG. 4 implementation. This can also be used in the embodiments of FIGS. 9-11; however, as with other specifics referred to herein, other types of implementations can be used. Absorbent material can be used with the detectors as described above. The sensor strip can be of uniform or varied width, and the moisture detector array can be uniformly distributed or located in selected areas. Multiple sensor strips 58 can be attached to the same connector 56. For the illustrated implementation having adjacent but electrically separate conductive paths, received moisture shorts the conductors to complete the otherwise open electrical circuit.

Figure 13:
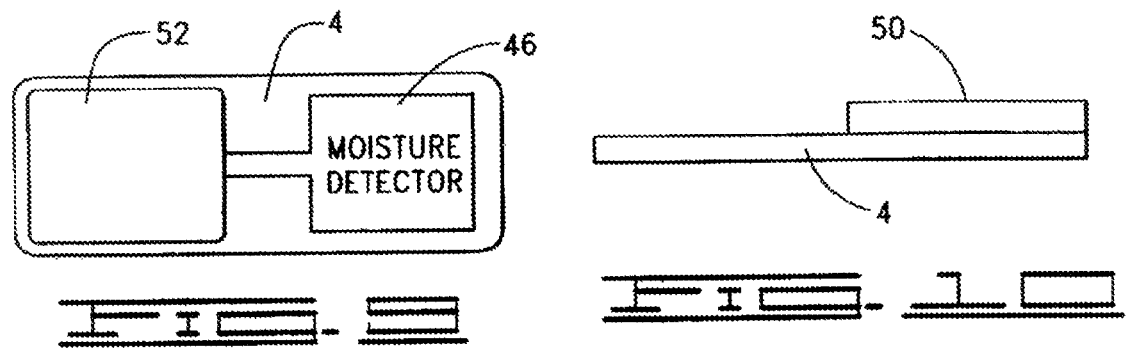
FIG. 13 is a perspective view of the sensing apparatus of FIG. 12 used with a diaper.

The moisture detector of FIG. 12 is shown in one application in FIG. 13. One or more moisture detectors are disposed in or on (either during manufacturing or after) a diaper 62. Each such connected moisture detector is flexible enough to conform to the diaper shape. The connector 56 shown in the drawings has its snap elements protrude through the diaper (such as snap connectors crimped through the diaper material) so that the electronics portion in housing or laminated substrate 64 snaps on the connector on the outside of the diaper 62.

The functions of sensing different conditions can be combined in one sensing apparatus 2. For example, the embodiment of FIG. 4 can sense both pressure and moisture. Pressure is sensed as described above, and moisture is sensed by communication of the moisture through the vent 14 to short the conductors 8a, 8b (the same type of shorting as occurs in the sensor of FIG. 12). Once moisture has been detected, the sensing apparatus typically is replaced. To prevent moisture sensing, conductors 8a, 8b can be sealed against moisture in a manner suitable to retain the flexibility, low profile and pressure sensitivity characteristics.

Figure 14:
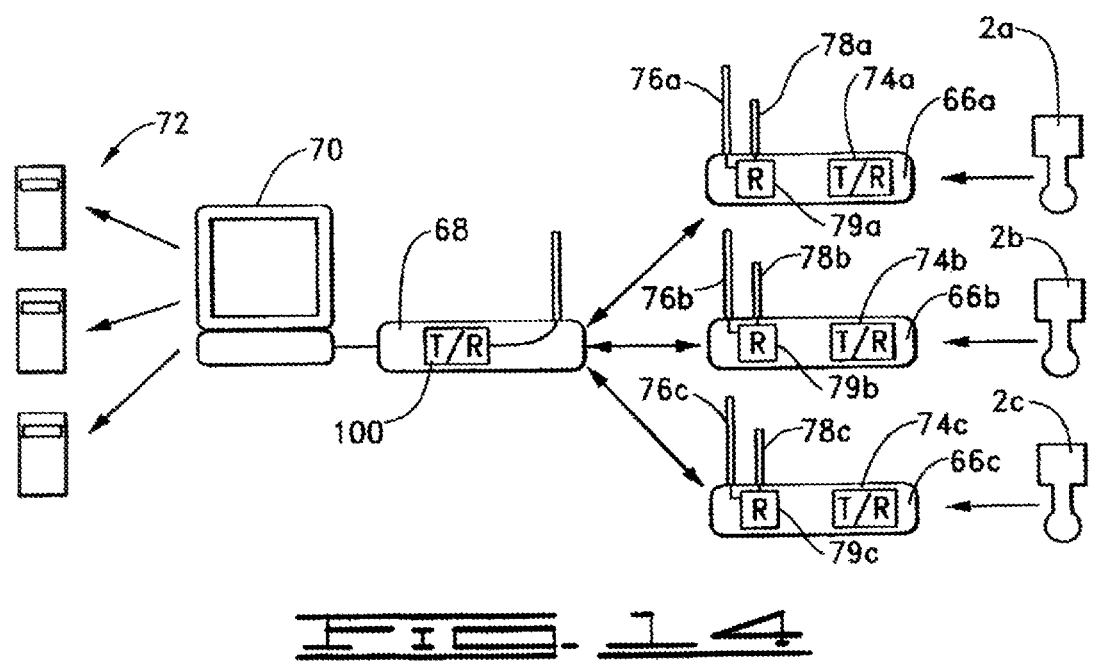
FIG. 14 illustrates a system of the present invention.

Referring next to FIG. 14, an embodiment of a system in which the sensing apparatus can be used is illustrated. One or more sensing apparatus 2 (three sensing apparatus 2a, 2b, 2c illustrated) are disposed on one or more patients who are in operative proximity to respective local (for example, bedside) monitors 66a, 66b, 66c that receive wireless communication signals from the respectively associated sensing apparatus 2a, 2b, 2c. Each bedside monitor 66 has bi-directional communication with a central (for example, ward) transceiver 68 connected to a computer 70, such as a personal computer (PC). The computer 70 is also illustrated as communicating with pagers 72.

Each bedside monitor 66 is configured to receive signals transmitted from the transmitter of each operatively associated sensing apparatus 2 such that the sensing apparatus 2 and the bedside monitor 66 are in wireless communication. The bedside monitor 66 includes a transceiver (T/R 74) having a receive antenna and a transmit antenna through which RF communications with the ward transceiver 68 occur. The bedside monitor 66 is located near the respective patient's bed (for example, within a 30-foot range), and it has two antennas 76, 78 (not necessarily external as illustrated, but shown this way for illustration) connected to a receiver 79 for receiving transmissions from one or more sensing apparatus 2. These antennas 76, 78 are automatically switched into the active receiver circuit 79 to receive transmissions from the sensing apparatus 2, thereby to avoid null spots as the sensing apparatus 2 is moved with movement of the patient (the illustrated transmitter on the sensing apparatus—as with many if not all antennas—does not have a true isotropic RF field so that a diversity antenna as described is needed to avoid null spots that a single receiving antenna would present).

When the bedside monitor 66 has received data via one of the sensing apparatus 2, the bedside monitor 66 in turn transmits to the central transceiver 68. In another example the bedside monitor can also store the received data until interrogated by the central transceiver 68. In a particular implementation, for example, this includes a bedside monitor ID and the respective sensor ID/status (for example, transmitted on a carrier frequency of 433.92 MHz at a power sufficient for up to a 500-foot range in a building, such as in a hospital or nursing facility).

FIG. 14 illustrates one exterior embodiment of a bedside monitor 66. This unit is powered either by battery or regulated "wall" current and has a 315 MHz receiver (to receive transmissions from the sensing apparatus) and a 433.92 MHz transceiver to communicate with the ward transceiver. The 315 MHz receiver can be controlled to have full or limited sensitivity. The bedside monitor 66 includes a central processing unit, such as a PIC16F877 microchip processor, for example. The bedside monitor has an address (ID) stored in nonvolatile memory. This ID is used by the ward transceiver 68 to address the transceiver 74 of the bedside monitor 66. The bedside monitor 66 has one or more suitable alarms (for example, an audible alarm or a visible alarm) to notify the patient or personnel in the vicinity. The bedside monitor 66 of FIG. 15 has three pushbuttons: an "away" mode button 80, a "service" button 82, and a "learn" button 84. The unit has but is not limited to two dual color (red/green) LEDs 86, 88 used to show the status of associated sensing apparatus (one or two sensing apparatus for this illustration "A" and "B"). The unit has two red LEDs 90, 92 to indicate low-battery state of the two associated sensing apparatus. The unit has an LED 94 to indicate "away" status, The unit has one red LED 96 above the service button. The unit has one red LED 98 to indicate low battery status of the bedside monitor 66 itself. Functionally, the program of this illustration provides the following capabilities:

The bedside monitor program receives sensing apparatus messages. It processes messages that match stored (learned) sensing apparatus IDs. Two IDs ("A" and "B") are stored in the illustrated embodiment. The program ignores messages from unknown sensing apparatus IDs.

The bedside monitor program displays the state of the two learned sensing apparatus on the corresponding dual-color status LEDs 86, 88. For example, if a message is received from a "learned" sensing apparatus 2 that the pressure switch ("A" for example) of FIG. 4 is closed, the red LED of the respective dual-color LED 86 (the "A" LED in our example)

is turned on. If it has received a message from the sensing apparatus 2 that indicates the pressure switch is open, then the green portion of the respective LED is lit. If no message has been received from the respective sensing apparatus 2 in two minutes, the respective status LED 86 or 88 will not be lit.

The bedside monitor program monitors the state of the batteries of the sensing apparatus 2. If a sensing apparatus low battery status bit in the encoded wireless transmission signal from the sensing apparatus 2 is set, the bedside monitor 66 lights the corresponding low battery LED 90 or 92. If this bit is cleared, the low battery light is extinguished.

When a sensing apparatus message is received, the status record in the bedside monitor 66 for the sensing apparatus 2 is updated with the present status, and the bedside monitor 66 time stamps the associated record with the time since the last ward transceiver status update. This time stamp is an 8-bit value representing seconds. If more than 240 seconds have elapsed, the value is clamped at 241 seconds.

When placed in the learn mode (by a user pressing the learn button 84), the bedside monitor 66 reduces its 315 MHz receiver sensitivity by at least 45 dB and waits for messages from a new sensing apparatus 2. It determines from these messages the new sensing apparatus ID, and whether it is an "A" or "B" for this example. The bedside monitor 66 sets a bit in its global status byte to indicate that a new sensing apparatus ID has been learned. This bit remains set until it is successfully read by the ward transceiver 68.

When interrogated by the ward transceiver 68 for state, the bedside monitor 66 transmits its state to the ward transceiver 68. This information includes: bedside monitor global status byte, two sensing apparatus time stamps, state bits for both sensing apparatus (encoded into two bytes), and the service timer value. If this information is correctly received by the ward transceiver 68, it sends an acknowledgement message to the bedside monitor 66. If the bedside monitor 66 receives an acknowledgment, it clears the global status bit indicating a new sensing apparatus and alarm silence, it clears the time stamps for both associated sensing apparatus, and it resets its time stamp clock.

When interrogated by the ward transceiver 68 for sensing apparatus IDs, the bedside monitor 66 transmits its global status byte and the two sensing apparatus IDs.

When commanded by the ward transceiver 68, the bedside monitor 66 activates its audible alarm. This alarm activation is a brief tone. When activated, the red LED 96 above the service pushbutton (service LED) comes on. When commanded by the ward transceiver 68, the bedside unit turns-off its service LED.

When the user depresses the "service" button 82, and if the service LED 96 is active, the service timer value is loaded with a time-stamp value and the service acknowledge bit is set in the global status byte. If the status of all active sensing apparatus 2 is "green," then the Service LED is extinguished.

The bedside monitor 66 monitors the state of its own battery. If a low battery status bit is set, the bedside monitor 66 lights its low battery LED 98.

If the user pushes the "away" pushbutton 80, the bedside monitor 66 enters the away mode. In this mode the unit extinguishes all its sensing apparatus status lights, sets the away hit in its global status byte, and lights the "away" LED 94. Normal sensing apparatus data processing is disabled, but bedside monitor battery and status processing operates normally. When the unit is in the away mode and the user pushes the "away" button 80, the unit returns to its normal mode.

The Global status byte has bits for: new sensing apparatus learned, low bedside monitor battery, away mode, audible alarm, and service acknowledged.

As represented in FIG. 14, the ward transceiver 68 is configured to receive wireless signals from and transmit signals to the transceivers 74 of the bedside monitors 66 (that is, the units 66, 68 preferably use wireless communication with each other). This ward transceiver 68 sends signals back to the corresponding bedside monitor 66 to indicate when predetermined conditions have been met (for example, if the duration where the sensing apparatus switch has remained closed has exceeded a pre-set period of time). This can cause the aforementioned visual or audible alarms to come on, or other functions can be implemented (e.g., turn on/off TV, control room lights, etc.; in general some action that causes the patient to alter the status of the sensing apparatus). In one particular implementation, the ward transceiver 68 includes a 433.92 MHz transceiver 100 to communicate with the bedside transceivers 74. The ward transceiver 68 has a serial port to communicate with the central computer 70. The ward unit of one implementation has a PIC16F877 processor. The ward transceiver 68 basically operates as a peripheral to the ward computer 70, translating PC (computer 70) serial messages into RF (radio frequency) transmissions, and RF receptions into serial messages to the ward PC. The ward transceiver maintains several status LEDs (power on, transmit, receive, data available and ward PC communication).

The ward transceiver 68 and the central computer 70 are located centrally (for example, at a nurses' station). One implementation of the computer 70 uses a Windows® based menu-driven interface (or other graphical user interface (GUI)—see FIG. 16 for one on-screen illustration) that allows input of 1) demographic data (for example, patient name, status of fecal/urinary incontinence, pressure ulcer risk level, additional risk factors, etc.): 2) device assignment data (bedside unit number, room number, pager number, etc.); and 3) notification parameters (turn and reposition time limits, local alarm candidate, toileting candidate, shift frequency limits, etc.). The monitoring program interrogates each bedside unit at one-minute intervals, for example, for bedside ID and associated sensor ID/status. The monitoring program associates date and time of occurrence for all system activities and status changes such as: sensor registration; change in sensor status (pressure on/off, dry/wet, low battery); sensor out of range. Algorithms programmed in the PC use input data from bedside units 66 to direct the system to execute specific actions for each patient based on notification parameters entered via the graphical user interface.

The ward PC program of one implementation resides on a Windows® based operating system. This system communicates with the ward transceiver 68 via an available serial port in the central computer 70. This implementation of computer 70 has a modem connected to a dial-up line for use in accessing the service provider for a commercially or proprietary/privately available pager service. The ward PC 70 fully controls all device and data activity associated with the illustrated system. This program can be written in any suitable programming language, two examples of which are VisualBasic® and VisualC®. The following functionality is in one embodiment of the ward PC program. It periodically interrogates bedside transceiver units. It displays present status of all beds on a single activity screen. It determines if state changes have occurred (for example, pressure/no pressure, dry/wet) and generates activity messages. These messages scroll on-screen and are written to an ASCII disk-logging file or Activity Record File for subsequent clinical or maintenance review or data manipulation. This record includes all events received from the bedside transceivers, periodically the state of all bedside transceivers, and, all local events (pager alarms, new setup information). From present state of sensing apparatus 2 and corresponding notification parameters, it determines if audible alarms should be generated. If so, it commands the respective bedside monitor to alarm. Furthermore, if required, it also sends alphanumeric text messages to pager units (using dial-up modem to contact pager service). It provides a single set-up screen for individual patients and allows entry of demographic, device assignment, and notification parameters as described above.

In the system of FIG. 14, the pagers 72 respond to control from the computer 70. Commercial or proprietary/private alphanumeric text pagers can be used. A suitably accessed pager can generate alarms and display messages on its liquid crystal display (LCD). All standard (model dependent) pager features such as low battery indication, alarm or vibrator configuration, message scrolling and suppression can be available to the user. When predetermined conditions are met, such as receipt of data indicating an episode of incontinence, the central PC 70 dials the appropriate number for a local paging service and transmits an alphanumeric text message to the designated user. The user is paged at ten-minute intervals until the wet diapers or other monitored condition(s) are changed. As an example, the following message: "Mr. Jones, room 111, 30 minutes", indicates that an incontinence episode occurred 30 minutes ago.

If the central computer 70 has capabilities for internet connection, this feature will enable the exchange and transmission of all data collected and generated by the present system through third party software commercially available.

Following are detailed data collection activities as performed by the central PC of the illustrated implementation:

For each bedside monitor the central PC records date and time for: 1) new sensor registration; 2) change in sensor status from dry to wet; 3) sensor out of range (if a registered sensor is moved beyond the reception range of the assigned bedside unit, the "out of range" status is transmitted to the Central PC and the activity record is updated accordingly; the "out of range" status is canceled upon the sensor's return to the bedside unit range).

The central PC calculates unprompted response time from onset of episode to when a new sensor was registered for each bedside monitor.

The ward monitor PC screen displays the following: patient name, room number, bed number (if applicable), bedside ID, current sensor serial number, and sensor status information.

In other embodiments, the bedside monitor (in addition or alternatively to the computer 70) contains programming to perform monitoring and management functions as desired. External data transfer from the bedside monitor can be provided for, such as via wired or wireless (for example, RF or optical) communication with an external data collection unit.

Thus, the present invention is well adapted to carry out the objects and attain the ends and advantages mentioned above as well as those inherent therein. While preferred embodiments of the invention have been described for the purpose of this disclosure, changes in the construction and arrangement of parts and the performance of steps can be made by those skilled in the art, which changes are encompassed within the spirit of this invention as defined by the appended claims.

What is claimed is:

1. Apparatus to sense a condition adjacent a human body, comprising:
    a sensor to sense a condition adjacent a human body, wherein the condition is at least one from the group consisting of a pressure occurring in response to weight of the human body against a support and moisture occurring from incontinence;
    a signal processing circuit to which the sensor connects;
    a transmitter connected to the signal processing circuit;
    a power supply connected to provide electricity for operation of the sensor, the signal processing circuit, and the transmitter; and
    a flexible printed circuit substrate having at least the signal processing circuit, the transmitter, and the power supply mounted thereon in low profile enabling disposition of the apparatus adjacent a human body.

2. Apparatus as defined in claim 1, wherein low profile of the apparatus is within a height of about 2 mm.

3. Apparatus as defined in claim 1, wherein the sensor is detachable from the signal processing circuit.

4. Apparatus as defined in claim 1, wherein the sensor is detachable from the signal processing circuit.

5. Apparatus as defined in claim 1, wherein the power supply includes biased contacts and an insulator disposed between the contacts to maintain the apparatus in a powered off state until the insulator is removed to allow the biased contacts to connect such that electricity is provided therethrough to operate the sensor, signal processing circuit and transmitter.

6. Apparatus as defined in claim 1, wherein the power supply includes a switch and transistors connected for maintaining a powered on state upon a one-time closure actuation of the switch.

7. Apparatus as defined in claim 1, further comprising a low power supply detector.

8. Apparatus to sense a condition adjacent a human body, comprising:
    a sensor to sense a condition adjacent a human body, wherein the condition is at least one from the group consisting of a pressure occurring in response to weight of the human body against a support and moisture occurring from incontinence;
    a transmitter configured to operatively associate with the sensor to transmit a signal digitally encoded with a unique identifier responsive to the sensor, the transmitter including an antenna; and
    a flexible substrate having the antenna disposed thereon and connected with the sensor and transmitter in low profile enabling disposition of the apparatus adjacent a human body.

9. Apparatus as defined in claim 8, further comprising a battery mounted on the flexible substrate for providing electricity to operate the sensor and the transmitter.

10. Apparatus as defined in claim 8, wherein low profile of the apparatus is within a height of about 2 mm.

11. Apparatus as defined in claim 8, further comprising a battery mounted on the flexible substrate for providing electricity to operate the sensor and the transmitter.

12. Apparatus as defined in claim 8, wherein the sensor is detachable.

13. Apparatus as defined in claim 8, further comprising a battery circuit including biased contacts and an insulator disposed between the contacts to maintain the apparatus in a powered off state until the insulator is removed to allow the biased contacts to connect such that electricity is provided therethrough to operate the sensor and transmitter.

14. Apparatus as defined in claim 8, further comprising a battery circuit that includes a switch and transistors connected for maintaining a powered on state upon a one-time closure actuation of the switch.

15. Apparatus as defined in claim 8, further comprising a low battery detector.

16. Apparatus to sense a condition adjacent a human body, comprising:

a sensor to sense a condition adjacent a human body, wherein the condition is at least one from the group consisting of a pressure occurring in response to weight of the human body against a support and moisture occurring from enuresis;

a transmitter configured to operatively cooperate with the sensor to transmit a signal responsive to the sensor;

a power supply for providing electricity to operate to the sensor and the transmitter, wherein the power supply includes a removable insulator film and a battery having a terminal initially electrically isolated from the sensor and transmitter by the insulator film such that the apparatus is energized by the battery upon pulling the insulator film out; and a flexible printed circuit substrate having at least the transmitter and the power supply mounted thereon in low profile enabling disposition of the apparatus adjacent a human body.

17. Apparatus as defined in claim 16, wherein low profile of the apparatus is within a height of about 2 mm.

18. Apparatus as defined in claim 16, wherein the sensor is detachable.

19. A method of sensing a condition adjacent a human body, comprising:

disposing in low profile adjacent a human body, by adhering to skin of the human body or by putting a diaper on the human body, apparatus to sense a condition adjacent the human body, the apparatus including a sensor, a transmitter, a power supply, and a flexible substrate having at least the transmitter and the power supply connected thereto in low profile enabling disposition of the apparatus adjacent a human body;

energizing the apparatus solely with the battery;

sensing a condition using the sensor, wherein the condition is at least one from the group consisting of a pressure occurring in response to weight of the human body against a support and moisture occurring from incontinence; and transmitting a wireless link signal from the transmitter in response to the sensed condition.

20. A method as defined in claim 19, further comprising storing unique identification data in the apparatus and transmitting a signal in response to the stored unique identification data.

21. A method as defined in claim 19, further comprising replacing the sensor without replacing the transmitter or the battery.

22. A method as defined in claim 19, wherein the sensor is disposable and wherein the method further comprises disconnecting the sensor from the transmitter and disposing of the sensor after sensing the condition, and connecting another disposable sensor to the transmitter to sense a subsequent condition.

23. A method as defined in claim 19, further comprising sensing a condition of the battery and transmitting in the wireless link signal data in response to the sensed condition of the battery.

24. A method as defined in claim 19, wherein transmitting is performed periodically.

25. A method as defined in claim 19, wherein transmitting is performed continuously.

26. Apparatus to sense a condition adjacent a human body, comprising:

a sensor to sense a condition adjacent a human body, wherein the condition is at least one from the group consisting of a pressure occurring in response to weight of the human body against a support and moisture occurring from incontinence;

a transmitter configured to operatively cooperate with the sensor to transmit a signal responsive to the sensor;

a power supply for providing electricity to operate to the sensor and the transmitter, wherein the power supply includes a battery, a switch and transistors connected for maintaining a powered on state upon a one-time closure actuation of the switch such that the apparatus is energized by the battery upon the one-time closure actuation; and a flexible printed circuit substrate having at least the transmitter and the power supply mounted thereon in low profile enabling disposition of the apparatus adjacent a human body.

27. Apparatus to sense a condition adjacent a human body, comprising:

a dual-mode sensor to sense both pressure and moisture adjacent a human body;

a signal processing circuit to which the sensor connects;

a transmitter connected to the signal processing circuit;

a power supply connected to provide electricity for operation of the sensor, the signal processing circuit, and the transmitter; and a flexible printed circuit substrate having at least the signal processing circuit, the transmitter, and the power supply mounted thereon in low profile enabling disposition of the apparatus adjacent a human body.

* * * * *